United States Patent
Ferrone

(10) Patent No.: US 7,550,568 B2
(45) Date of Patent: Jun. 23, 2009

(54) MONOCLONAL ANTIBODIES TO HUMAN HIGH MOLECULAR WEIGHT-MELANOMA ASSOCIATED ANTIGEN

(75) Inventor: Soldano Ferrone, Buffalo, NY (US)

(73) Assignee: University of Pittsburgh - Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 12/039,282

(22) Filed: Feb. 28, 2008

(65) Prior Publication Data

US 2008/0214791 A1 Sep. 4, 2008

Related U.S. Application Data

(63) Continuation of application No. 11/746,519, filed on May 9, 2007, now abandoned, which is a continuation of application No. 10/307,757, filed on Dec. 2, 2002, now abandoned.

(60) Provisional application No. 60/334,368, filed on Nov. 30, 2001.

(51) Int. Cl.
*C07K 16/00* (2006.01)
*A61K 38/00* (2006.01)
*C07K 14/00* (2006.01)
*C07K 17/00* (2006.01)
*C07K 2/00* (2006.01)
*C07K 4/00* (2006.01)
*C07K 5/00* (2006.01)

(52) U.S. Cl. .................... 530/387.7; 530/300; 530/350; 530/380; 530/385; 530/387.1; 530/387.2; 530/388.1; 530/388.15; 530/389.7; 530/391.1; 530/391.5; 424/130.1; 424/141.1; 424/142.1; 424/152.1; 424/155.1; 424/178.1; 424/156.1; 514/1; 514/2; 514/8; 514/12

(58) Field of Classification Search ............ 530/388.15, 530/300, 350, 380, 385, 387.1, 387.7, 388.1, 530/387.2, 389.7, 391.1, 391.5; 424/130.1, 424/141.1, 142.1, 152.1, 155.1, 156.1, 178.1; 514/1, 2, 8, 12

See application file for complete search history.

*Primary Examiner*—Alana M. Harris
(74) *Attorney, Agent, or Firm*—Klarquist Sparkman, LLP

(57) ABSTRACT

The present invention provides monoclonal antibodies that react against high molecular weight melanoma-associated antigen. These antibodies may be used for diagnostic and/or therapeutic purposes.

11 Claims, No Drawings

MONOCLONAL ANTIBODIES TO HUMAN HIGH MOLECULAR WEIGHT-MELANOMA ASSOCIATED ANTIGEN

CROSS REFERENCE TO PRIOR APPLICATIONS

This application is a continuation of U.S. patent application Ser. No. 11/746,519, filed May 9, 2007 now abandoned, which is a Continuation of U.S. patent application Ser. No. 10/307,757, filed Dec. 2, 2002 now abandoned, which claims priority to U.S. provisional application No. 60/334,368, filed on Nov. 30, 2001, the disclosure of which is incorporated herein by reference.

FIELD OF THE INVENTION

This invention relates generally to the field of antibodies and more particularly to monoclonal antibodies to the human high molecular weight-melanoma associated antigen.

BACKGROUND OF THE INVENTION

Melanomas are tumors of the skin, less frequently of mucous membranes, some of which are benign. Malignant melanomas are carcinomas of neuroectodermal origin generally derived from melanocytes (pigment-producing cells), sometimes from mucous membranes, the chorioid coat or the meninges. There are several types of malignant melanoma which differ in localization, way of spreading and production of metastases.

Conventional treatment of melanoma includes surgery, radiation or chemotherapy, and the application of biological response modifiers. However, these methods have proven to be insufficient to prevent tumor recurrence, and are complicated by significant side effects. Therefore, it is desirable to develop therapeutic approaches which overcome these drawbacks and can replace or be used in combination with conventional treatment.

Since the immune system seems to be heavily involved in the pathogenesis of this disease, attention has now turned to active immunotherapy, for example based on specific antigens. In melanoma, an example of suitable targets for the production of antibodies and the development of immunotherapeutic approaches are the melanoma associated antigens (MAA), a number of which have been identified and characterized by their molecular weight, for example high molecular weight-melanoma associated antigen (HMW-MAA) with a molecular weight of >1,000,000.

Although not immunogenic in patients with melanoma, HMW-MAA is expressed in at least 80% of melanoma lesions; has a restricted tissue distribution; patients with melanoma possess an immune repertoire that recognizes this antigen and is considered to play a role in the metastatic potential of melanoma.

SUMMARY OF THE INVENTION

The invention provides monoclonal antibodies and/or antibody fragments to human high molecular weight melanoma associated antigens. The antibodies or fragments thereof may be used for diagnosis of melanoma or for therapeutic purposes. The invention also provides hybridoma cell lines which produce the monoclonal antibodies specific for the HMW-MAA.

DESCRIPTION OF THE INVENTION

This invention provides monoclonal antibodies or antibody fragments to melanoma associated antigens. The antibodies or fragments thereof may be used for diagnosis of melanoma and/or for therapeutic purposes.

The term "antibody fragments" as used herein for purposes of the specification means a portion or fragment of the intact antibody molecule wherein the fragment retains antigen binding function. Examples of such fragments include $F(ab')_2$, Fab', Fab, Fv, scFv, Fd' and Fd fragments. Method for producing various fragments are well known to those skilled in the art.

For preparation of the antibodies, the High Molecular weight-Melanoma Associated Antigen (HMW-MAA) bearing human melanoma cells can be used. The cells can be incubated with IFN-γ. Animals may be immunized with whole cells, cell lysates or purified HMW-MAA. Animals suitable for immunization include mice, rats, rabbits and goats.

Immunogenic conjugates of HMW-MAA can be prepared by standard methods known in the art such as by adsorption of the immunizing antigen to the carrier or by coupling using periodate, glutaraldehyde, carbodiimides e.g. N,N'-o-phenylenedimaleirnide, N-(-m-maleimidobenzoyloxy)-succinimide, N-(3->2'-pyridyldithio!-propionoxy)-succinimide, N-ethyl-N'-(3-dimethyl aminopropyl)-carbodiimide or the like. A commonly used conjugate is involves conjugating the antigen to keyhole limpet haemocyanin (KLH) with glutaraldehyde.

The immunogen may be mixed with adjuvants, i.e. agents which will further increase the immune response, for the immunization procedure. Examples of suitable adjuvants are Freund's complete adjuvant (emulsion of mineral oil, water, and mycobacterial extracts), Freund's incomplete adjuvant (emulsion of water and oil only), mineral gels, e.g. aluminum hydroxide gels, surface active substances such as lysolecithin, polyanions, peptides, BCG (*Bacillus Calmette-Guerin*), etc.

Immunization can be carried out by standard routes of immunization including intradermal, subcutaneous, intramuscular, intraperitoneal, intravascular and intracranial injections. Since high antibody titers are desired, a series of injections is commonly given. The immunization is for example performed by injecting the antigen two, three, four or more times parenterally, e.g. intraperitoneally and/or subcutaneously, in regular or irregular intervals of a few days, e.g. three to seven days, up to several months, for example four weeks.

After immunization, the antibody producing cells may be recovered from the immunized animal. The antibody producing cells may be spleen cells or lymph node derived B cells. Antibody-producing cells recovered from the immunized mice, preferably lymphoid cells such as spleen lymphocytes, taken for example one to five days after the final injection, are fused with the cells of a continuous cell line, i.e. a continuously replicating cell clone which confers this replication ability to the hybrid cells resulting from the fusion. An example for such a cell line is a tumor cell line (myeloma) which does not itself actually produce inununoglobulins or fragments thereof but has the potential to produce and secrete large amounts of antibody, and which carries a genetic marker so that the hybrid cells can be selected against non-fused parent cells. Several suitable myeloma cell lines are known in the art. Preferred are myeloma cell lines lacking the enzyme hypoxanthine guanine phosphoribosyl transferase (HGPRT) or the enzyme thymidine kinase (TK), which therefore do not survive in a selective culture medium containing hypoxanthine, aminopterin and thymidine (HAT medium). Particularly preferred are myeloma cells and derived cell lines that do not survive in HAT medium and do not secrete immunoglubulins or fragments thereof, such as the cell lines P3×63Ag8.653 or Sp2/0-Ag14.

The fusion is performed in the presence of a fusion promoter, for example Sendai virus or other paramyxo viruses, optionally in UV-inactivated form, or chemical fusogens such as calcium ions, surface-active lipids, e.g. lysolecithin, or polyethylene glycol (PEG), or by electrofusion. Preferentially, the myeloma cells are fused with a three- to twentyfold excess of spleen cells from immunized mammals in a solution containing about 30% to about 60% of polyethylene glycol of a molecular weight between 1000 and 4000.

After the fusion, the cells are resuspended and cultivated in a selective medium chosen depending on the genetic selection marker, for example HAT medium. In this medium, only hybridoma cells will survive, because they combine the ability to grow and replicate in vitro inherited from the parent myeloma cells and the missing HGPRT or TK genes essential for the survival in HAT medium inherited from the antibody-producing spleen cells of the immunized mammals.

Suitable culture media for the expansion of hybridoma cells are the standard culture media, such as Dulbecco's Modified Eagle Medium (DMEM), minimum essential medium, RPMI 1640 and the like, optionally replenished by a mammalian serum, e.g. 5% to 15% fetal calf serum. The culture media are supplemented with selective medium in order to prevent myeloma cells from overgrowing the hybridoma cells. The supernatant of the hybridoma cells can be screened for the monoclonal antibodies. For example, hybridomas may be selected from the fused cells by radioimmunoassay, enzyme-labeled immunoassay (ELISA), fluorescence labeled immunoassays or the like using HMW-MAA.

Positive hybridoma cells are cloned, e.g. by limiting dilution or in soft agar, preferentially twice or more. Optionally, hybridoma cells are passaged through animals, e.g. mice, by intraperitoneal injection and harvesting of ascites, which stabilizes hybridomas and improves growth characteristics. The cloned cell lines may be frozen in a conventional manner. In a preferred embodiment, hybridomas producing the monoclonal antibodies TP109 and VF20-VT1.7 were produced. These hybridomas were deposited at the American Type Culture Collection (ATCC) as ATCC Accession No. PTA 9582 (murine hybridoma VF4 TP109.2) and ATCC Accession No. PTA 9583 (murine hybridoma VF20-VT.1), respectively, in accordance with the Budapest Treaty on Nov. 4, 2008.

Also provided in this invention are the hybridoma cell lines which secrete the monoclonal antibodies of the present invention. In particular, the invention provides hybridoma cell lines which are hybrids of myeloma cells and B lymphocytes of a mouse immunized with a monoclonal antibody directed against high molecular weight-melanoma associated antigen. Preferentially, these cell lines are hybrids of mouse myeloma cells and B lymphocytes of a mouse, for example a Balb/c mouse, immunized with melanoma cells. Especially preferred is the hybridoma cell line which secretes monoclonal antibody TP109 and the hybridoma cell line which secretes the monoclonal antibodies VF20-VT1.7. The hybridoma cell lines of the invention may be kept in deep-frozen cultures and reactivated by thawing and optionally re-cloning.

The invention also provides pharmaceutical compositions comprising a monoclonal antibody and/or a fragment thereof according to the invention. The pharmaceutical compositions comprise, for example, the monoclonal antibodies and/or fragments thereof in a therapeutically effective amount together or in admixture with a pharmaceutically acceptable carrier.

The antibodies of the present invention may be used for diagnostic and therapeutic purposes. The antibodies of the present invention can be used for qualitative or quantitative detection of melanoma and other tumor cells. The detection is carried out by standard immunological methods well known in the art. The antibodies obtained according to the present invention can thereby be used as such or may be labeled or conjugated (such as to toxins). Thus, the monoclonal antibodies can be used for tumor targeting The antibodies according to the present invention can also be used for the progress of a treatment regimen or as a prognostic indicator. After treatment of a melanoma patient by conventional treatments such as radiation etc., the antibodies of the present invention can be used to determine the presence of the antigen in the body fluids. The level of the antigen may also be determined following treatment.

The present invention also provides a process for the diagnosis or therapy of tumors and especially of melanomas, wherein there is administered one or a mixture of several antibodies according to the present invention, optionally together with conventional pharmaceutical carrier, adjuvant, filling and additive materials.

The antibodies of the present invention have the characteristics as described in the examples given below. The following examples are presented for illustrative purposes and are not intended to be restrictive.

EXAMPLE 1 mAb TP109

For this antibody, a BALB/c mouse was immunized four times at 2 week intervals with intramuscular injections of $3 \times 10^6$ cultured human melanoma cells Colo38 which had been incubated with IFN-γ (final concentration 1000 U/ml) for 48 hours at 37° C. Spleen cells were obtained from the immunized mouse and fused with murine myeloma cells Ag8.X.653. Hybridizations and subcloning were performed according to standard procedures. The supernatant from the hybridomas was tested for reaction with melanoma cells Colo 38. A positive reacting hybridoma, labeled herein as TP109 was identified. The supernatant of this hybridoma reacted with Colo 38 cultured human melanoma cells but not with cultured human B lymphoid cells LG2 as determined by ELISA.

When tested with a panel of cultured human melanoma cells in a binding assay, mAb TP109 reacted with HMW-MAA bearing human melanoma cells but did not react with cultured human B lymphoid cells and with cultured human carcinoma cells. The latter two types of cells do not express HMW-MAA. Furthermore, mAb TP109 immunoprecipitated from radiolabeled cultured human melanoma cells Colo 38 components with the characteristic electrohpretic profile of HMW-MAA when analyzed by SDS-PAGE.

EXAMPLE 2 mAb VF20-VT1.7 and VT68.2

For these antibodies a BALB/c mouse was immunized five times at 3 week intervals with intramuscular injections of approximately 200 µl of a bead suspension. The bead suspension had been preincubated with a NP40 lysate of $1 \times 10^7$ cultured human melanoma Colo 38 cells. Spleen cells were obtained from the immunized mouse and fused with murine myeloma cells Ag8.X.653. Hybridizations and subcloning were performed according to standard procedures. The supernatants from the hybridomas were tested for reaction with melanoma cells Colo 38. The hybridomas, VF20-VT1.7 and VT68.2 were found to react with cultured human melanoma cells Colo38, but not with cultured human B lymphoid cells LG2 in a binding assay.

When tested with a panel of cultured human melanoma cells in a binding assay, mAbs VF20-VT1.7 and VT68.2 reacted with HMW-MAA bearing human melanoma cells but did not react with cultured human B lymphoid cells and with cultured human carcinoma cells. Furthermore, mAb VF20-VT1.7 and VT68.2 immunoprecipitated from radiolabeled cultured human melanoma cells Colo 38 components with the characteristic electrohpretic profile of HMW-MAA when analyzed by SDS-PAGE.

It will recognized by those skilled in the art that routine modifications to the methods and compositions presented here are possible. Such modifications are intended to be within the scope of this invention.

The invention claimed is:

1. A monoclonal antibody which specifically binds to human high molecular weight melanoma associated antigen (HMW-MAA) bearing human melanoma cells but not to human B lymphoid cells, wherein the monoclonal antibody is designated as TP109 ATCC Accession No. PTA-9582.

2. A monoclonal antibody, which specifically binds to human high molecular weight melanoma associated antigen (HMW-MAA) bearing human melanoma cells but not to human B lymphoid cells, wherein the monoclonal antibody is designated as VF20-VT1.7 ATCC Accession No. PTA-9583.

3. A pharmaceutical composition comprising the monoclonal antibody of claim 1 or 2.

4. The pharmaceutical composition of claim 3, wherein the monoclonal antibody is TP109.

5. The pharmaceutical composition of claim 3, wherein the monoclonal antibody is VF20-VT1.7.

6. A hybridoma producing the monoclonal antibody of claim 1.

7. A hybridoma producing the monoclonal antibody of claim 2.

8. The monoclonal antibody of claim 1, wherein the monoclonal antibody is a F(ab')$_2$, FAb', Fab, Fv, scFv, Fd' or a Fd fragment.

9. The monoclonal antibody of claim 2, wherein the monoclonal antibody is a F(ab')$_2$, FAb', Fab, Fv, scFv, Fd' or a Fd fragment.

10. A composition comprising an effective amount of the monoclonal antibody of claim 8 and a carrier.

11. A composition comprising an effective amount of the monoclonal antibody of claim 9 and a carrier.

* * * * *